US00PP20469P2

(12) United States Plant Patent
Bourquin

(10) Patent No.: US PP20,469 P2
(45) Date of Patent: Nov. 10, 2009

(54) ***PHOTINIA* PLANT NAMED 'BOURFRITS'**

(50) Latin Name: *Photinia×fraseri*
Varietal Denomination: Bourfrits

(76) Inventor: Andre Bourquin, 2 Kms Rarbe-route de Bordeaux, 65320 Borderez sur Lechez (FR)

( * ) Notice: Subject to any disclaimer, the term of this patent is extended or adjusted under 35 U.S.C. 154(b) by 0 days.

(21) Appl. No.: 12/231,559

(22) Filed: Sep. 4, 2008

(51) Int. Cl.
*A01H 5/00* (2006.01)

(52) U.S. Cl. ..... Plt./226

(58) Field of Classification Search ..... Plt./226
See application file for complete search history.

(56) References Cited

OTHER PUBLICATIONS

UPOV-ROM PBR 20070560, published Jun. 15, 2007.*

* cited by examiner

*Primary Examiner*—Annette H. Para
*Assistant Examiner*—Louanne C Krawczewicz Myers
(74) *Attorney, Agent, or Firm*—Penny J. Aguirre

(57) ABSTRACT

A new cultivar of *Photinia,* 'Bourfrits', characterized by its bushy, compact, mounded plant habit, its stems that are supple, slightly arching, and well branched with short internode lengths, and its leaves that form a rosette at the growing tips when emerging, have strongly serrated margins, and are bright red in color when young.

2 Drawing Sheets

Botanical classification: *Photinia×fraseri.*
Variety denomination: 'Bourfrits'.

BACKGROUND OF THE INVENTION

The present invention relates to a new and distinct cultivar of *Photinia×fraseri*, and will be referred to hereafter by its cultivar name, 'Bourfrits'. 'Bourfrits' is a new cultivar of deciduous shrub for use as a landscape plant.

The new cultivar of *Photinia* was derived from a controlled cross made by the inventor using self-pollination of *Photinia* 'Red Robin' (not patented) in 1994 at his nursery in Borderez Sur Lechez, France. The inventor lined out the resulting seedlings in a trial bed and 'Bourfrits' was selected as unique by the inventor in summer of 1997.

Asexual reproduction of the new cultivar was first accomplished using terminal stem cuttings by the inventor in in Borderez Sur Lechez, France in summer of 1997. The characteristics of this cultivar have been determined to be stable and are reproduced true to type in successive generations.

SUMMARY OF THE INVENTION

The following traits have been repeatedly observed and represent the characteristics of the new cultivar as grown outdoors in a test plot for ten years in Borderez Sur Lechez, France. These attributes in combination distinguish 'Bourfrits' as a unique cultivar of *Photinia* that is unlike any other cultivars of *Photinia* known to the inventor.

1. 'Bourfrits' is freely branched with a bushy plant habit producing an open mound with its height nearly equal to its spread.
2. 'Bourfrits' exhibits stems that are supple and slightly arching.
3. 'Bourfrits' exhibits a compact habit with short internode lengths between branches.
4. 'Bourfrits' produces small leaves that form a rosette at the growing tips above the stems when emerging.

5. 'Bourfrits' exhibits leaves that are bright red in color and have margins that are strongly serrated.

The closest comparison plant to 'Bourfrits' is the parent plant 'Red Robin'. 'Red Robin' differs from 'Bourfrits' in having a more oval and less compact plant habit, in having less branches that are more upright and stiff with longer internode lengths, and in having leaves that are larger, darker red in color, and have less serration on the margins. 'Bourfrits' can also be compared to the cultivar 'Parred' (U.S. Plant Pat. No. 17,665). 'Parred' is similar in being well branched, however 'Parred' differs from 'Bourfrits' in having an upright plant habit and leaves that are larger, obovate in shape, and darker red in color.

BRIEF DESCRIPTION OF THE DRAWING

The accompanying colored photographs illustrates the overall appearance and distinct characteristics of 3 year-old plants of the new *Photinia* as grown outdoors in 15 cm. containers in Borderez Sur Lechez, France.

The photograph is

Figure 1:
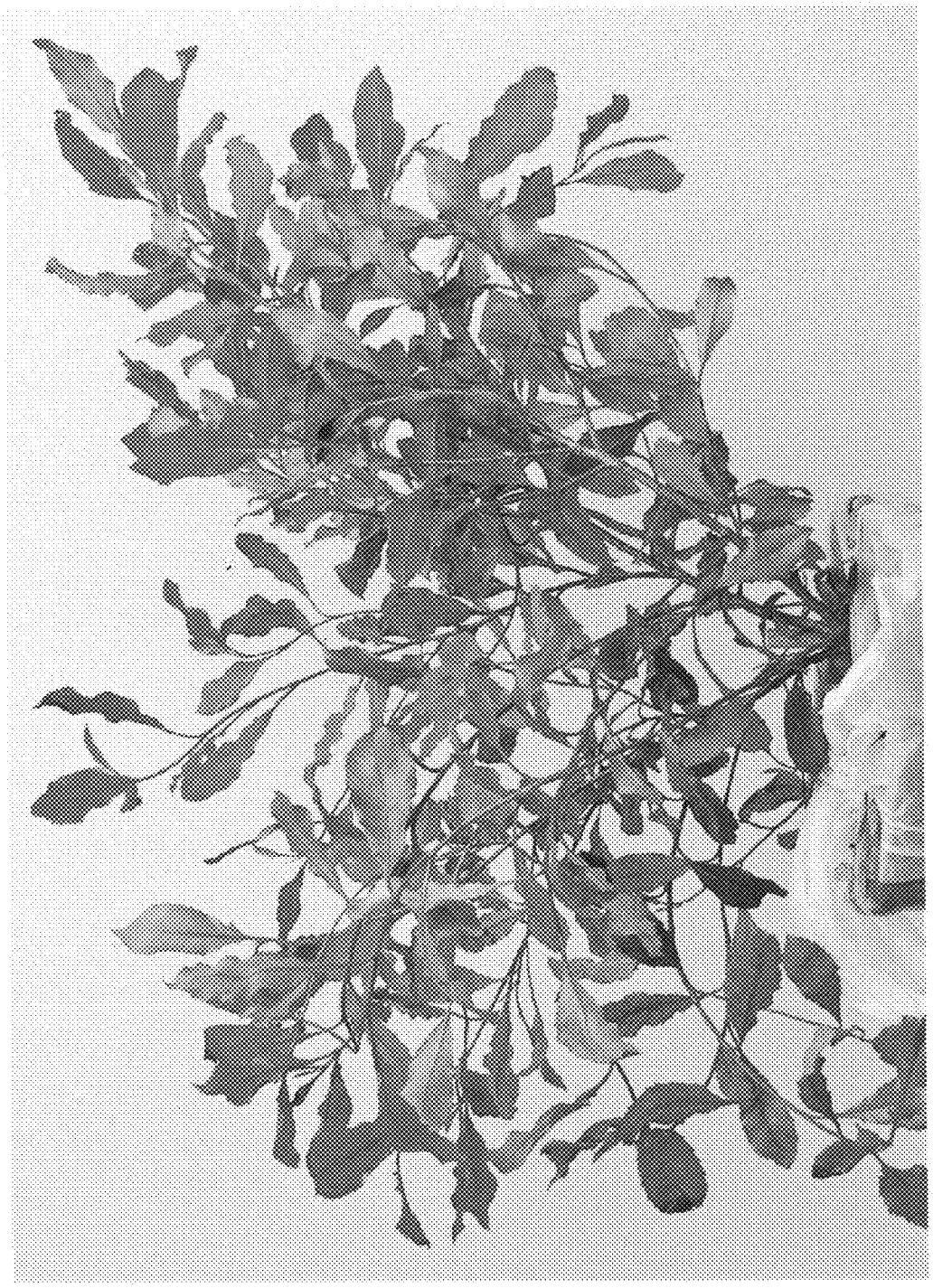
FIG. 1 is a side view and illustrates the overall habit and changing foliage coloration of 'Bourfrits'.
Figure 3:
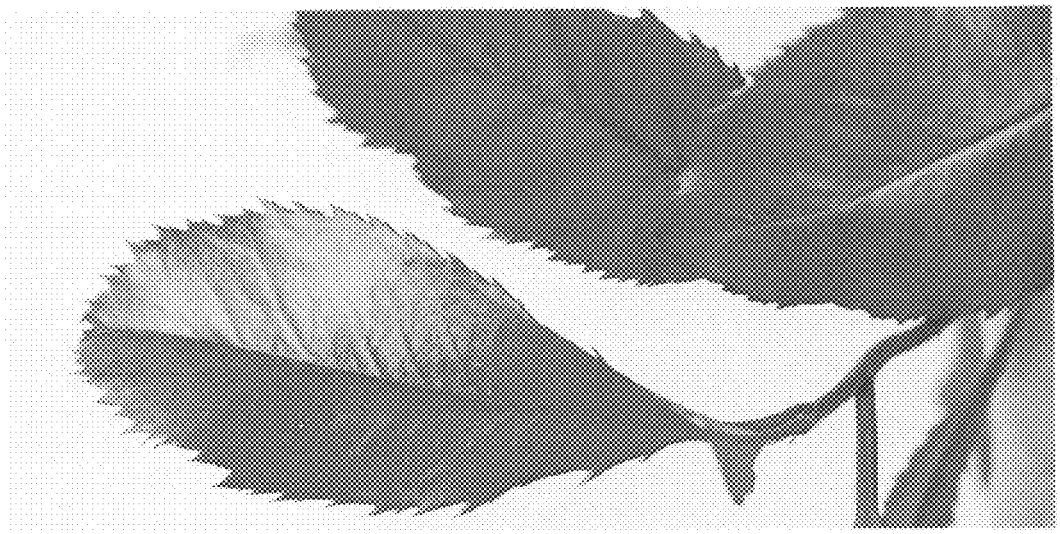
Figure 2:
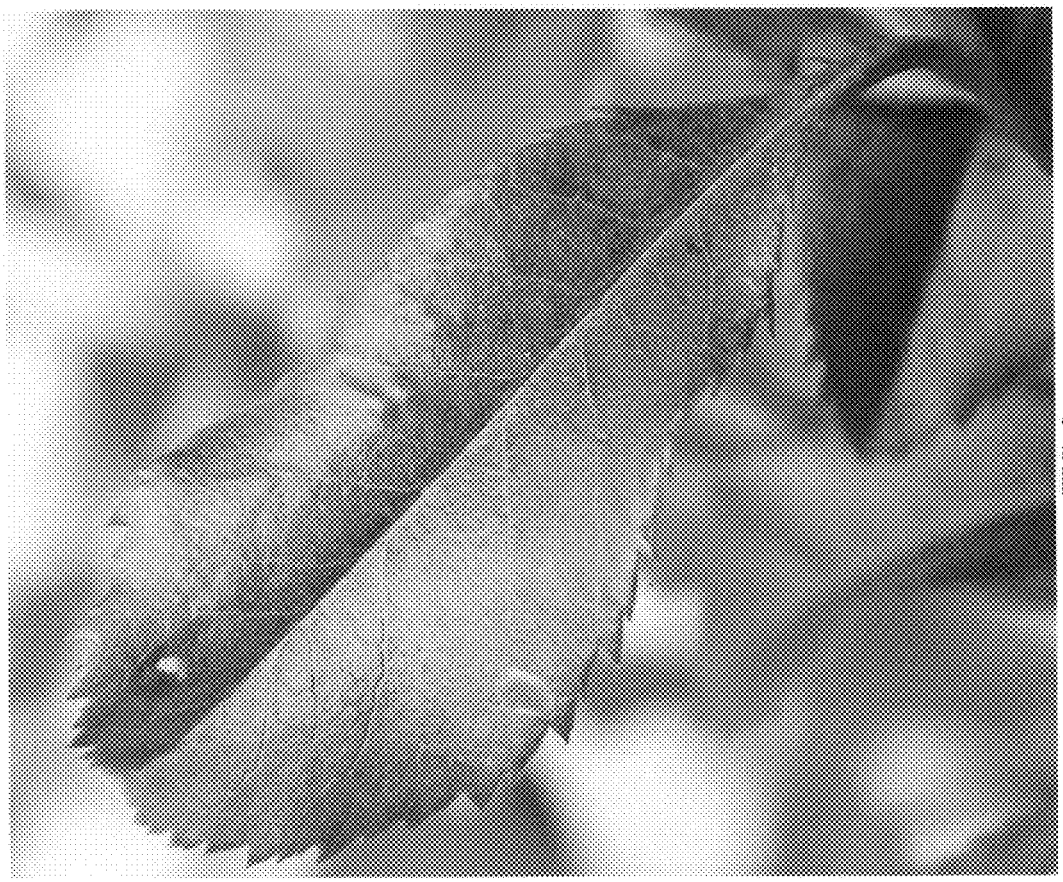

The photograph in FIG. 2 provides a close-up view of the mature foliage of 'Bourfrits' and the photograph in FIG. 3 provides a close-up view of the young foliage of 'Bourfrits'.

The colors in the photograph are as close as possible with the digital photography techniques available and the color values cited in the detailed botanical description most accurately describe the colors of the new *Photinia.*

DETAILED BOTANICAL DESCRIPTION

The following is a detailed description of 3 year-old plants of the new *Photinia* as grown outdoors in 15 cm containers in Borderez Sur Lechez, France. The phenotype of the new cultivar may vary with variations in environmental, climatic, and cultural conditions, as it has not been tested under all possible environmental conditions. The color determination is in accordance with the 2001 RHS Colour Chart of The Royal Horticultural Society, London, England, except where general color terms of ordinary dictionary significance are used.

General description:

*Plant type.*—Deciduous, perennial shrub.

*Plant habit.*—Compact, bushy, open mound.

*Height and spread.*—Average of 54 cm. in height and 60 cm. in height in a 25 cm. container and reaches up to 1.5 m in height and width when mature.

*Cold hardiness.*—At least to U.S.D.A. Zone 7a.

*Diseases and pests.*—No susceptibility or resistance to diseases or pests has been observed.

*Root description.*—Fibrous.

*Propagation*—Half-ripe terminal stem cuttings.

*Growth rate.*—Moderate.

Stem description:

*Shape.*—Rounded, strong.

*Stem color.*—New twigs; 180A, mature bark; color between N187A and N200A.

*Stem size.*—Lateral branches average 27 cm. in length and an average of 2.5 mm. in diameter.

*Stem surface.*—Glossy, no pubescence.

*Branching.*—Freely branched; average of 31 lateral branches.

*Branch internode length.*—Average of 2.3 cm.

Foliage description:

*Leaf shape.*—Obovate.

*Leaf division.*—Simple.

*Leaf base.*—Attenuate.

*Leaf apex.*—Apiculate.

*Leaf fragrance.*—None.

*Leaf venation.*—Pinnate, 137B to 137C in color on upper surface and 152A to 152B in color on lower surface.

*Leaf margins.*—Serrate and wavy.

*Leaf arrangement.*—Alternate.

*Leaf attachment.*—Petiolate.

*Leaf number.*—Average of 12 per lateral branch.

*Leaf surface.*—Upper surface and lower surface; glossy, glabrous and smooth.

*Leaf size.*—Average of 7 cm. in length and 2.9 cm. in width when mature with young leaves an average of 3.5 cm. in length and 1.25 cm. in width.

*Leaf internode length.*—Average of 2.3 cm.

*Leaf color.*—Newly expanded leaves upper surface; 178A and 183A but slightly more brownish, newly expanded leaves lower surface; 181A, mature leaves upper surface; 137A and 147A, mature leaves lower surface; 146C to 146D.

*Petioles.*—Average of 1.3 cm. in length and 1.5 mm. in width, N183A, 187B and 187C in color, surface is glossy.

*Stipules.*—Non observed.

Flower description: Flowering has not been observed.

It is claimed:

1. A new and distinct cultivar of *Photinia* plant named 'Bourfrits', as herein illustrated and described.

* * * * *